United States Patent
Cantu et al.

(10) Patent No.: US 8,545,426 B2
(45) Date of Patent: Oct. 1, 2013

(54) SYSTEM AND METHOD FOR CONTROLLING PATIENT FLUID BALANCE AND/OR FLOW RATE FOR A THERAPEUTIC PLASMA EXCHANGE PROCEDURE

(75) Inventors: Robert J. Cantu, West Chester, OH (US); Timothy J. Patno, Barrington, IL (US); Timothy A. Johnson, Issaquah, WA (US); David L. Bonnett, Reading, MA (US); Russell D. Stinaff, Chicago, IL (US); Carole Lynn Stinaff, legal representative, Chicago, IL (US)

(73) Assignee: Fenwal, Inc., Lake Zurich, IL (US)

( * ) Notice: Subject to any disclaimer, the term of this patent is extended or adjusted under 35 U.S.C. 154(b) by 827 days.

(21) Appl. No.: 12/394,340

(22) Filed: Feb. 27, 2009

(65) Prior Publication Data
US 2010/0168639 A1   Jul. 1, 2010

Related U.S. Application Data

(60) Provisional application No. 61/031,724, filed on Feb. 27, 2008.

(51) Int. Cl.
*A61M 1/14* (2006.01)
(52) U.S. Cl.
USPC .......................................... 604/4.01; 210/646
(58) Field of Classification Search
USPC .................................. 604/4.01, 5.01; 210/646
See application file for complete search history.

(56) References Cited

U.S. PATENT DOCUMENTS

| | | | | |
|---|---|---|---|---|
| 5,178,603 | A * | 1/1993 | Prince | 604/6.01 |
| 5,910,252 | A * | 6/1999 | Truitt et al. | 210/645 |
| 6,471,872 | B2 * | 10/2002 | Kitaevich et al. | 210/739 |
| 6,585,675 | B1 * | 7/2003 | O'Mahony et al. | 604/4.01 |
| 7,438,705 | B2 * | 10/2008 | Karpowicz et al. | 604/313 |
| 2001/0037079 | A1 * | 11/2001 | Burbank et al. | 604/6.09 |
| 2006/0124548 | A1 * | 6/2006 | Okazaki | 210/646 |

OTHER PUBLICATIONS

Operator's Manual of Spectra Optia Apheresis System from Gambro BCT, Inc., Lakewood, Colorado dated 2007.

* cited by examiner

*Primary Examiner* — Susan Su
(74) *Attorney, Agent, or Firm* — Cook Alex Ltd.

(57) ABSTRACT

Systems and methods for controlling fluid flow during a fluid exchange procedure. In one aspect, a system is provided for controlling a net fluid volume difference of a patient during and/or after a fluid exchange procedure. The system comprises a first flow path for flowing at least a first fluid from the patient and a second flow path for flowing at least a second fluid to the patient. First and second reservoirs are respectively associated with the first and second flow paths. A controller is associated with the first and second flow paths for controlling first and second flow rates and operable to determine an actual flow rate for each first and second fluid and to change a first or second flow rate in response to a difference between at least one of such flow rates and its respective actual flow rate.

8 Claims, 7 Drawing Sheets

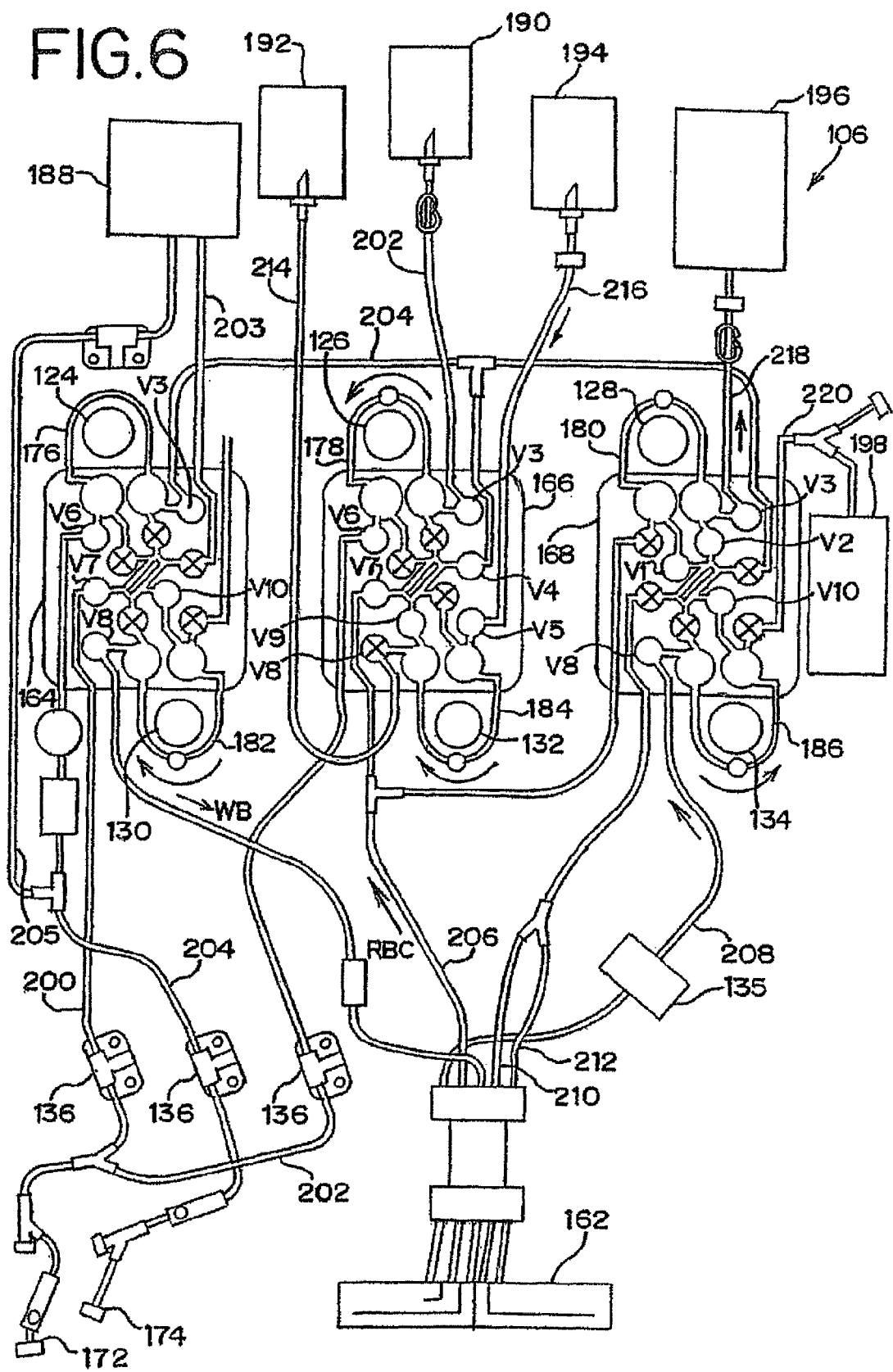

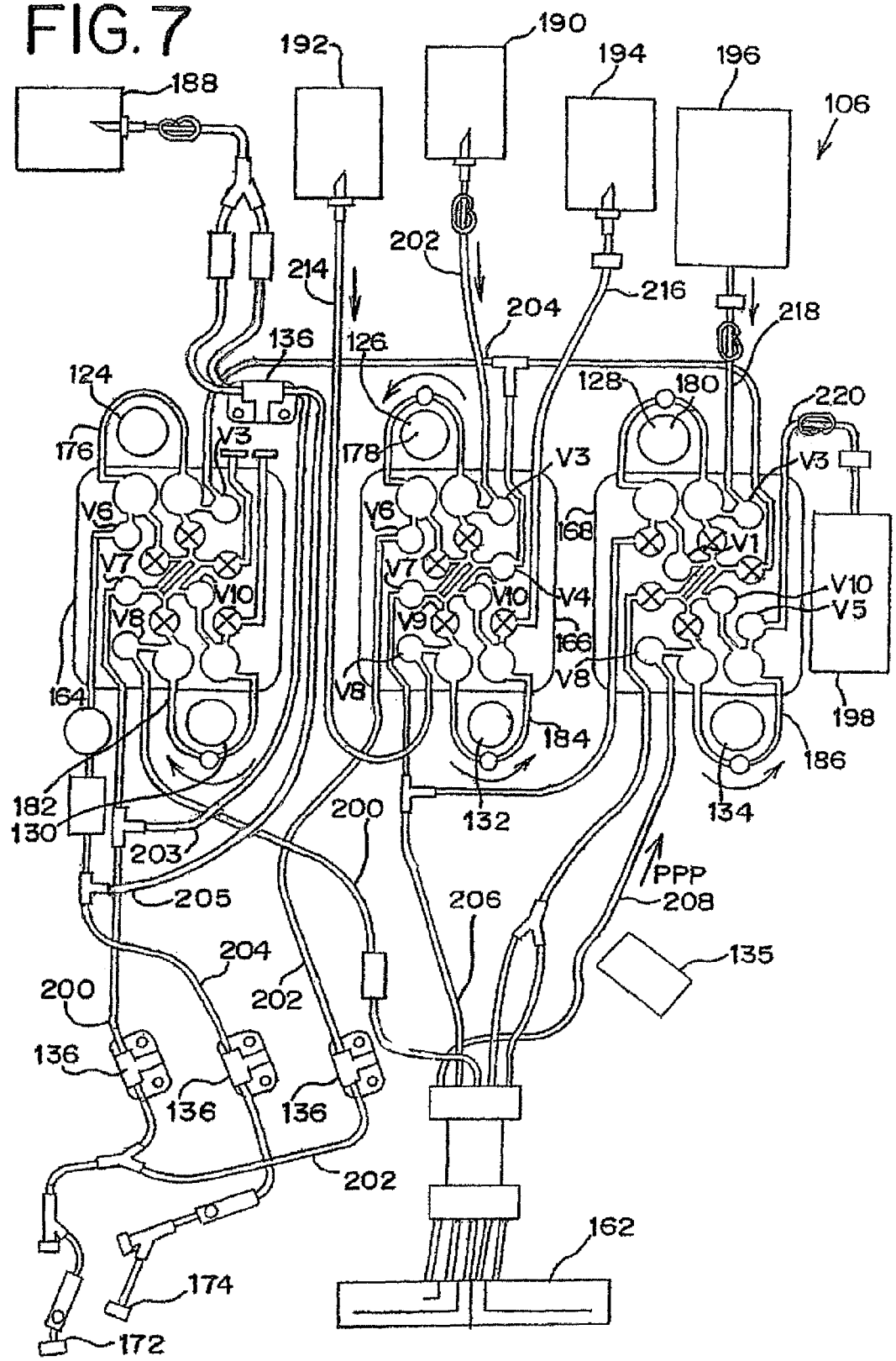

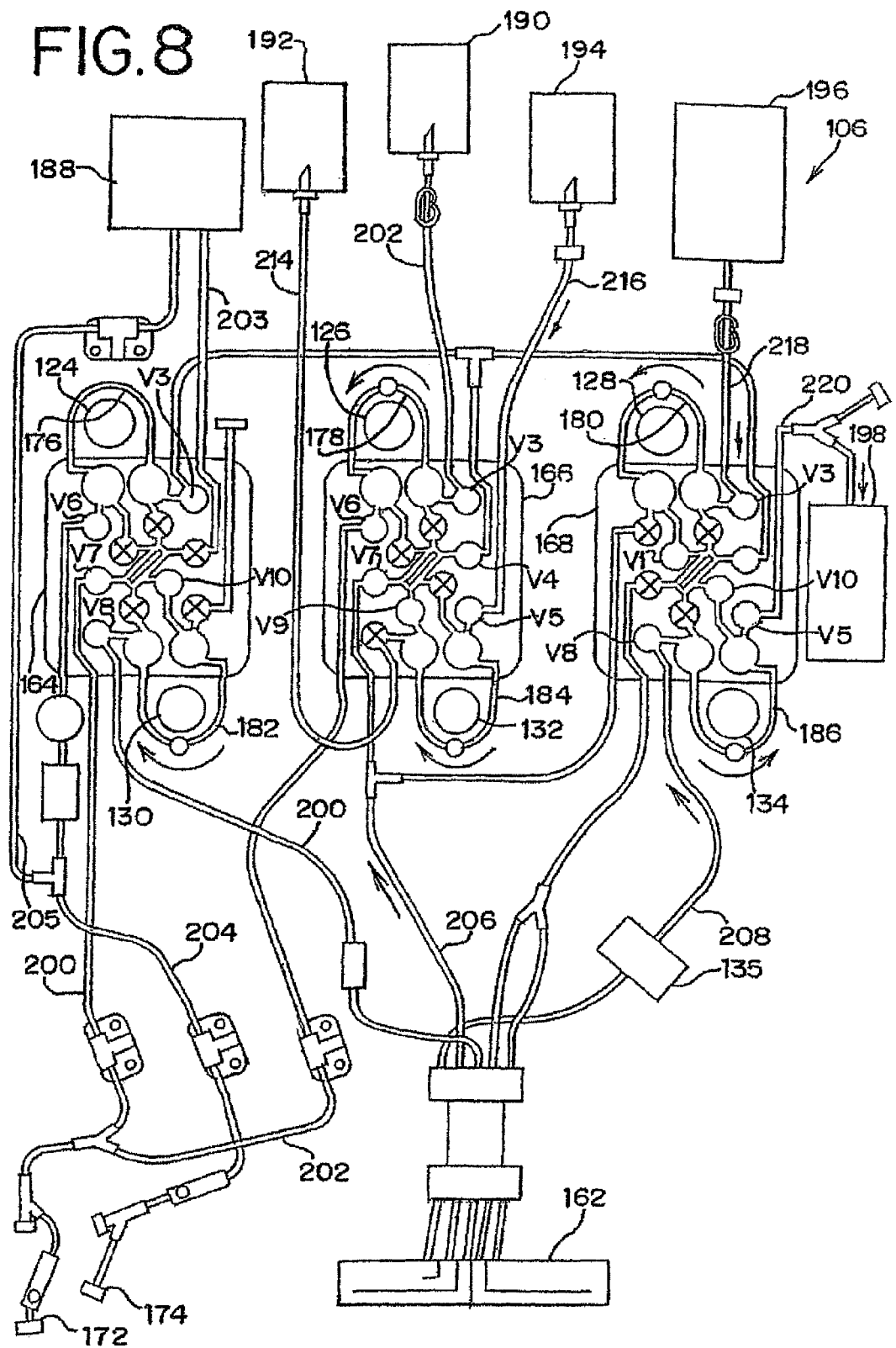

SYSTEM AND METHOD FOR CONTROLLING PATIENT FLUID BALANCE AND/OR FLOW RATE FOR A THERAPEUTIC PLASMA EXCHANGE PROCEDURE

CROSS-REFERENCE TO RELATED APPLICATION

This application claims the benefit of U.S. Provisional Patent Application Ser. No. 61/031,724, filed on Feb. 27, 2008, the disclosure of which is hereby incorporated herein by reference.

BACKGROUND

This disclosure generally relates to a biological fluid processing system and method thereof. More specifically, this disclosure relates to a system and method for a therapeutic fluid exchange procedure that exchanges at least one constituent component, such as a blood component, withdrawn from a patient with one or more replacement fluids that are infused to the patient.

Blood processing systems and methods that relate to a therapeutic exchange procedure typically involves withdrawal of a biological fluid, such as whole blood, from a patient and replacement with another fluid. The biological fluid, such as whole blood, withdrawn from the patient may be directed to a separator, such as a centrifugal or membrane assembly, for separation of at least one constituent component, such as at least one blood component or, for example, red blood cells, plasma and/or platelets. Depending on the procedure, certain separated constituent components may be retained by the system and not returned to the patient. The remaining separated constituent components may be returned to the patient together with one or more replacement fluids. The particular separated constituent that is not returned to the donor may depend on the specific medical needs of the patient. For example, one type of therapeutic exchange procedure is a plasma exchange procedure that removes a quantity of separated plasma from withdrawn whole blood of a patient and returns to the patient at least one replacement fluid, such as fresh plasma or other fluid, along with the remaining separated blood components.

In therapeutic exchange procedures, however current systems may lack the desired consistency to maintain a desired fluid balance, and inaccuracies may lead to a fluid balance drift within the patient such that the patient receives either too much or too little replaced fluid, which can be of concern for any patient, but particularly, pediatric patients, who may require maintaining a fluid balance within a desired range. Thus, there is a continuing need to provide a system and/or method that provides control of the fluid balance of a patient and/or the fluid flow relative to such patient during and/or after a therapeutic exchange procedure, or for other use in applications in other fields.

SUMMARY

In one aspect, the present disclosure is directed to a system for controlling a net fluid volume difference of a patient during and/or after a medical fluid exchange procedure. The system may include a first flow path for flowing at least a first fluid from the patient and a second flow path for flowing at least a second fluid to the patient. First and second reservoirs may be respectively associated with the first and second flow paths. A controller may be associated with the first and second flow paths for controlling the flow of the first and second fluids at respective first and second commanded flow rates. The controller may be operable to determine an actual flow rate for each of the first and second fluids based, at least in part, on an actual volume difference respectively measured relative to the first and second reservoirs over a time period. The controller may be operable to change at least one of the first and second commanded flow rates in response to a difference between at least one of the first and second commanded flow rates and its respective actual flow rate so as to achieve a net fluid volume difference of the patient. The system may further be operable to control the net fluid volume difference within a desired range.

In another aspect, the present disclosure is directed to a system for controlling a flow rate of at least one fluid flowing during a fluid exchange procedure. The system may include a first flow path for flowing at least a first fluid from a patient and a second flow path for flowing at least a second fluid to the patient. First and second reservoirs may be respectively associated with the first and second flow paths. A controller may be associated with the first and second flow paths for controlling the flow of the first and second fluids. Such a controller may be operable to determine a commanded flow rate of at least one of the first and second fluids based, at least in part, on a calculated volume of such first or second fluid that flows through its respective flow path over a time period. The controller may be further operable to determine an actual flow rate of such first or second fluid based, at least in part, on an actual volume difference respectively measured relative to the first or second reservoir over such time period. The controller may also be operable to change such commanded flow rate in response to a difference between the commanded flow rate and the actual flow rate to achieve a desired flow rate. The system may be particularly useful in a procedure wherein one of the first and second fluids comprises primarily plasma and the other of the fluids includes a replacement fluid.

In a further aspect, the present disclosure is directed to a method for controlling a net fluid volume difference of a patient during and/or after a medical fluid exchange procedure. The method may include monitoring a first flow rate of at least a first fluid removed from the patient and a second flow rate of at least a second fluid flowing to the patient. The method may also include determining an actual flow rate for each of the first and second fluids, based, at least in part, on an actual volume of such first fluid removed from the patient and such second fluid flowing to the patient. The method may further include changing at least one of the first and second flow rates so as to achieve a desired net fluid volume difference of the patient.

In yet another aspect, the present disclosure is directed to a method for controlling a flow rate of at least one fluid flowing during and/or after a medical fluid exchange procedure. The method may include determining a commanded flow rate of at least one of a first fluid flowing to a patient or a second fluid flowing from a patient based, at least in part, on a calculated volume of such first or second fluid that flows over a time period. The method may also include determining an actual flow rate of such first or second fluid based, at least in part, on an actual volume of such first or second fluid that respectively flows over such time period. The method further may include changing the commanded flow rate of such first or second fluid in response to a difference between the commanded flow rate and the actual flow rate to achieve a desired flow rate. The method may be particularly useful in a procedure wherein one of the first and second fluids comprises primarily plasma and the other of the fluids includes a replacement fluid.

BRIEF DESCRIPTION OF THE DRAWINGS

FIG. 6 is a diagrammatic view of a disposable set, similar to FIG. 5, showing an alternate flow pattern.

FIG. 7 is a diagrammatic view of a disposable set, similar to FIG. 5, showing another flow pattern.

FIG. 8 is a diagrammatic view of a disposable set, similar to FIG. 5, showing yet a further flow pattern.

DETAILED DESCRIPTION

Figure 1:
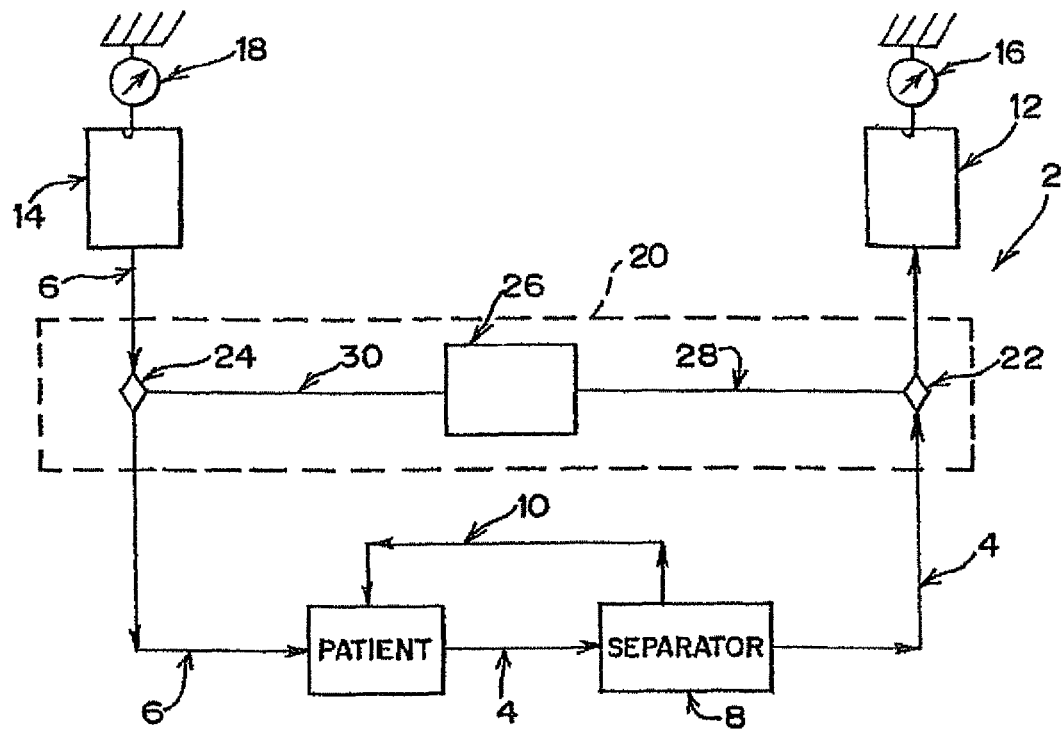
FIG. 1 is a diagrammatic view of one embodiment of a processing system that is set forth in the present disclosure.

In accordance with one embodiment of the present disclosure, FIG. 1 illustrates a processing system, generally indicated at 2, that can be used for processing various fluids. The system 2 may be particularly well suited to processing whole blood and/or other suspensions of biological fluids. Although the processing of whole blood will be described, the illustrated embodiments are not limited to such processing and may be employed for processing other biological fluids. By way of example and not limitation, the systems described herein are employed for a therapeutic plasma exchange procedure during which plasma is separated from withdrawn whole blood, and the remaining blood components and a replacement plasma or fluid are returned to a patient. It is understood that the systems described herein are not limited to such procedure and that other procedures are also possible.

Figure 2:
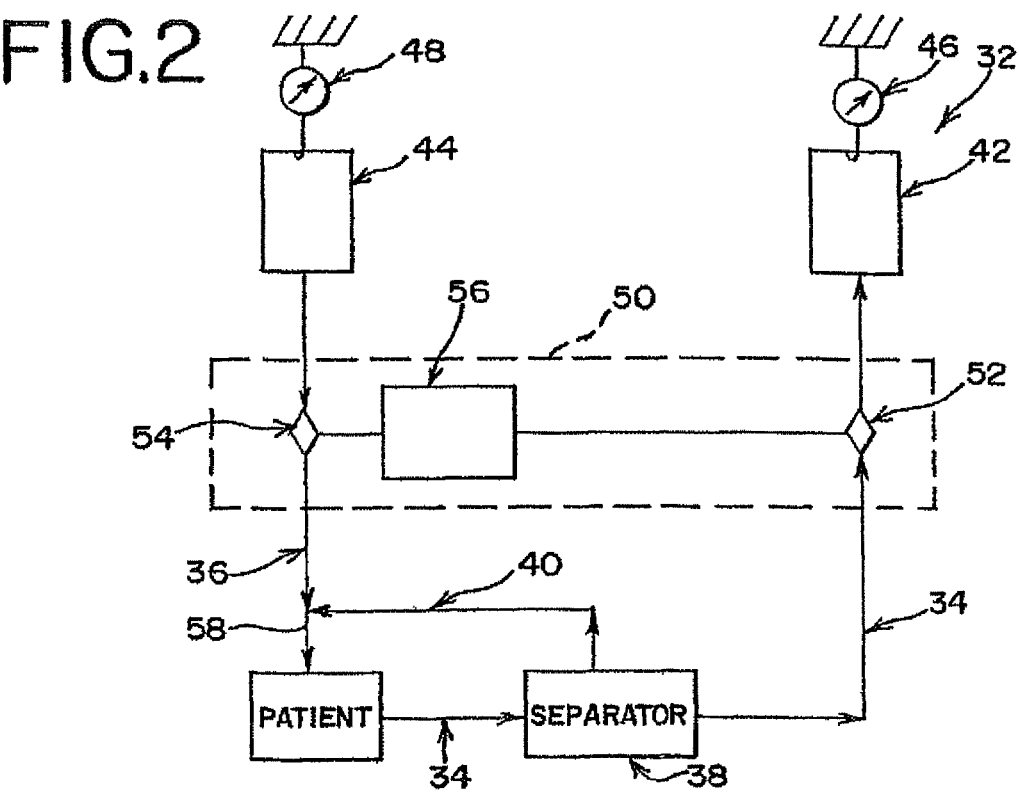
FIG. 2 is a diagrammatic view of another embodiment of a processing system that is set forth in the present disclosure.

In FIG. 1, the system 2 includes, among other things, a first flow path and a second flow path, generally indicated at 4 and 6, respectively. The first flow path 4 preferably communicates with a patient for flowing at least a first fluid from the patient. In FIG. 1, the first fluid preferably includes plasma that is withdrawn from the patient as part of withdrawn whole blood and subsequently separated from the remaining blood components. The second flow path 6 preferably communicates with the patient for flowing at least a second fluid to the patient. In FIG. 1, the second fluid preferably includes a replacement fluid, such as fresh plasma or other medical fluids, depending on the desired procedure to be performed. It is also possible that the second flow path may provide for a mixture of the replacement fluid and one or more of the remaining blood components, such as red blood cells, white blood cells and/or platelets, to flow to the patient, such as shown in FIG. 2.

In FIG. 1, a separator, generally indicated at 8, may be associated with the first flow path 4 for separating withdrawn whole blood from the patient into one or more separated blood components. By way of example, the separator 8 may separate primarily plasma from the remaining blood components, e.g., red blood cells, platelets and white blood cells. In FIG. 1, the separated plasma flows downstream of the separator 8 through the first flow path 4. A return flow path, generally indicated at 10, preferably allows the remaining blood components to flow from the separator 8 for return to the patient.

In FIG. 1, the separated plasma preferably flows from the separator 8 to a first reservoir, generally indicated at 12. In FIG. 1, the first reservoir 12 is preferably associated with the first flow path 4 at a downstream end of such flow path 4. A second reservoir, generally indicated at 14, is preferably associated with the second flow path 6 and is more preferably located at an upstream end of such path 6. The second reservoir 14 preferably stores the replacement fluid that may flow through the second flow path 6 to the patient. Each first and second reservoir 12 and 14 is also preferably associated with a sensing mechanism for determining the volume or amount of fluid in each reservoir. Any suitable sensing mechanism may be used, and as illustrated the first and second reservoirs are each associated with a respective weight scale, generally indicated at 16 and 18 respectively. The reservoirs 12 and 14 may be attached to such scales 16 and 18 by a hook or other suitable attachment so as to monitor the weight or change in weight of such reservoirs and their contents during and/or after the procedure.

In FIG. 1, a controller, generally indicated at 20, may incorporate one or more devices that are associated with the first and second flow paths 4 and 6 for controlling the flow of the separated plasma and the replacement fluid. By way of example and not limitation, the controller 20 may include first and second flow controllers, such as pumps, generally indicated at 22 and 24. The pumps 22 and 24 are preferably respectively associated with the first and second flow paths 4 and 6 for respectively controlling fluid flow of the plasma and the replacement fluid. By way of example, the pumps 22 and 24 may be peristaltic pumps although it is understood that other types of flow controllers, including but not limited to other diaphragm pumps and/or valves as well as gravity-controlled flow controllers, are possible.

The controller 20 may further include a main controller, such as a programmable controller, generally indicated at 26, that is operatively associated with the first and second pumps 22 and 24 for controlling such pumps. In FIG. 1, the controller 26 may control the pumps 22 and 24 by way of one or more control pathways, lines or wires, such as generally indicated at 28 and 30, or by wireless connection. The controller 26 is preferably operable to determine and/or control the respective flow rates of the plasma and the replacement fluid in accordance with other aspects discussed below.

In accordance with another embodiment of the present disclosure, FIG. 2 illustrates another system, generally indicated at 32. Similar to FIG. 1, the system 32 in FIG. 2 includes a first flow path 34, a second flow path 36, a separator 38, a return flow path 40, first and second reservoirs 42, 44, first and second weight scales 46, 48, a controller 50, first and second pumps 52 and 54 and a main controller 56. In FIG. 2, the second flow path 36 and the return flow path 40 communicate with the patient using a combined flow path 58. Although the paths are shown as joined at a selected location downstream of the pump 54, it is understood that other locations are also possible.

Figure 3:
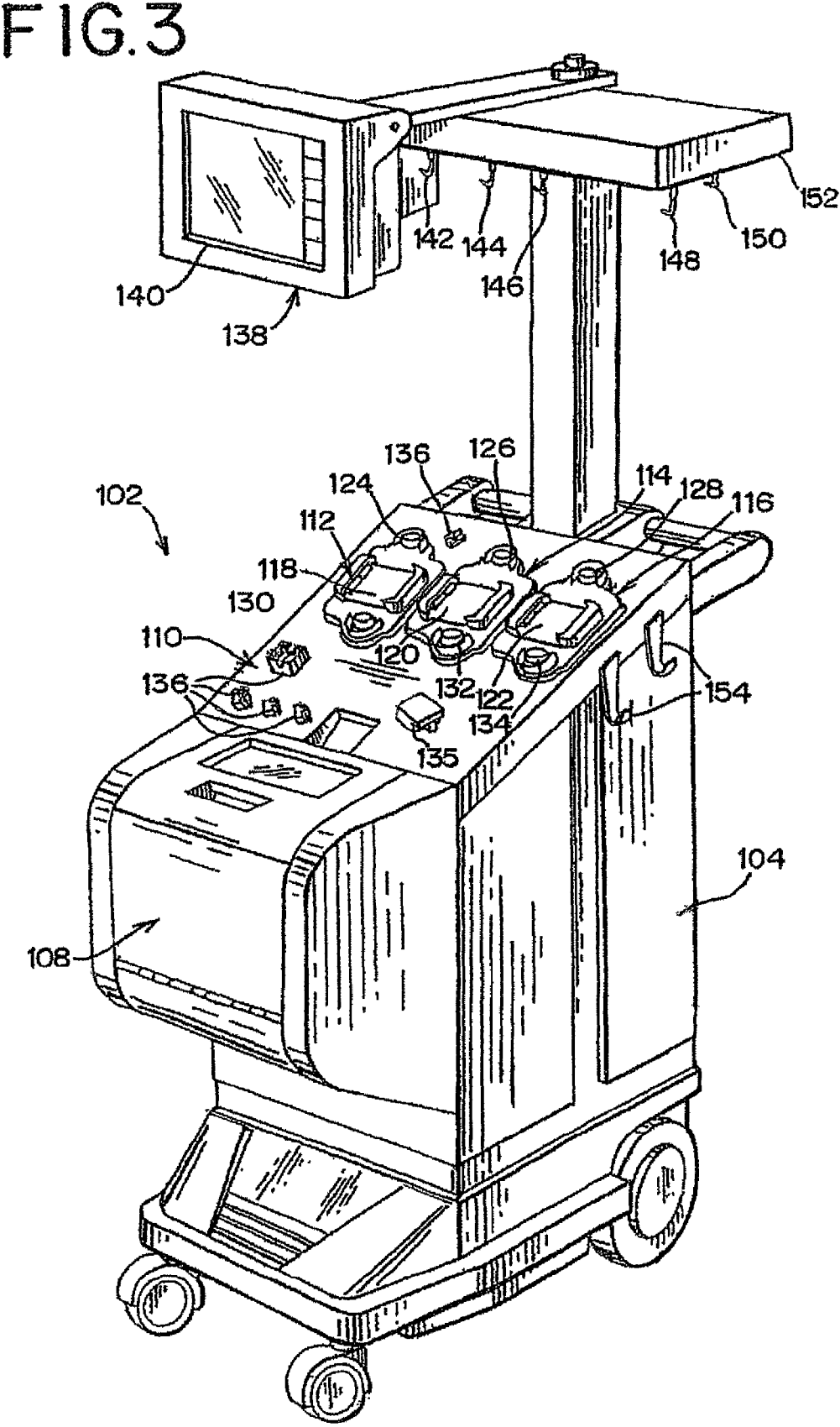
FIG. 3 is a perspective view of one embodiment of a centrifugal processing device that may be employed in a system that is set forth in the present disclosure.

In accordance with a further and more specific embodiment, FIG. 3 illustrates a centrifugal processing device, generally indicated at 102, that can be used for processing various fluids. The device 102 is part of a system employing a disposable, pre-assembled and pre-sterilized fluid processing set (FIG. 4) that operates in cooperation with the durable reusable hardware device 102 for carrying out the method for controlling patient fluid balance described herein. The illustrated embodiment is substantially identical to a commercial centrifuge sold by Fenwal, Inc. as the Amicus® separator, which is disclosed in numerous patents and patent applications, not limited to but including U.S. Pat. No. 5,868,696, to Giesler et al, issued Feb. 9, 1999, which is incorporated herein by reference. It is understood that the present disclosure is not limited to such a device or to the processing of whole blood, and that the present disclosure may have application in a variety of settings where processing of biological fluid is desired.

Figure 4:
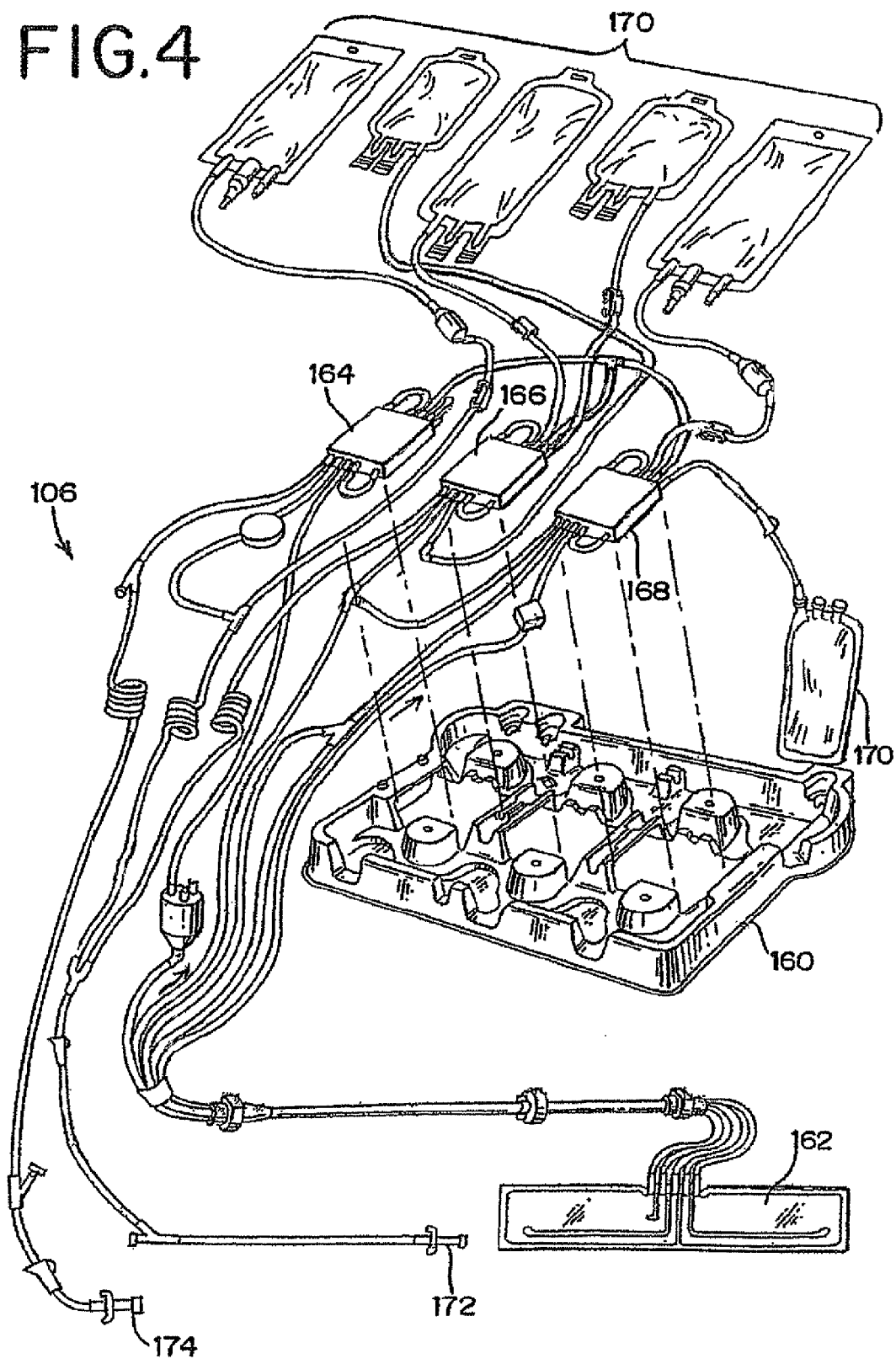
FIG. 4 is an exploded perspective view of a disposable fluid processing set usable in association with the processing device shown in FIG. 3.

In FIG. 3, the centrifugal processing device 102 includes a separation assembly, generally within the housing indicated at 104, and a disposable fluid processing set in FIG. 4, generally indicated 106, used in association with the processing device 102. As noted above, the separation assembly need not be a centrifugal processing assembly, such as that disclosed and shown in U.S. Pat. No. 5,868,696, and other separation technology or devices, such as membrane separators, may also be used. The separation assembly 104 receives and separates a biological fluid, such as whole blood and/or other biological fluids, into two or more constituent components. The separation assembly 104 is preferably adapted to be durable and reusable over a long term. The fluid processing set 106 (described in more detail later), in contrast, is preferably disposable and a fresh sterile set may be assembled with the separation assembly 104 for each use.

In FIG. 3, the separation assembly 104 includes an access compartment, generally indicated at 108, which houses a portion of the disposable set 106, such that when the separation assembly 104 is activated, the constituent components are separated within such portion of the set 106. A panel, generally indicated at 110, provides a surface for receiving another portion of the disposable set 106. For example, the panel 110 includes three pumping and valving stations, or respective left, middle and right stations, generally indicated at 112, 114, and 116, in FIG. 3. Each station 112, 114 and 116 respectively includes a valve interface portion 118, 120, 122, an upper flow controller or pump 124, 126, 128 and a lower flow controller or pump 130, 132, 134. As described above, each pump 124, 126, 128, 130, 132, 134 may be a peristaltic pump adapted to be associated with a section of tubing to provide flow control. The panel 110 may further include a detector 135, such as an optical detector, and/or other sensors or clamps, generally indicated at 136, for controlling and/or monitoring fluid and/or air flow in the disposable set 106.

In FIG. 3, the system 102 further includes a controller, generally indicated at 138. The controller 138 may be a programmable controller that is operable to control the system 102 for various processes. An operator interface module 140 may allow for viewing of the past, current and/or upcoming operations and/or provide for operator input by way of a touch screen and/or one or more tactile controls. One or more weight scales 142, 144, 146, 148, 150 may be associated with the controller 138. In FIG. 3, such scales may be attached to a platform or stand 152 that allows one or more fluid containers to be attached to or hung from the scales and to allow for weight measurement of such containers during and/or after the processing procedure. One or more hooks 154 may also extend downwardly from a right or left side of the panel 110 to allow attachment of other fluid containers and may also be associated with a weight scale, if desired.

The disposable set 106 employed with the durable hardware component 102 is illustrated in FIG. 4 and is adapted to be loaded onto the separation assembly 104 in FIG. 3. Prior to use, the set 106 may be organized into a tray 160 in FIG. 4 that is preferably hermetically sealed and sterile. The set 106 in FIG. 4 shows a double needle (one for withdrawal of fluid from a patient and one for return of fluid to the patient) processing assembly although it is understood that the present disclosure is not limited to double needle processing and may include single needle and other types of processing sets.

In FIG. 4, the set 106 includes a processing chamber 162, left, middle and right pumping and valving cassettes 164, 166 and 168, one or more fluid reservoirs or containers 170, a draw needle 172 and a return needle 174. FIG. 4 also shows various tubing paths that will be discussed in further detail relative to FIGS. 5-8.

Figure 5:
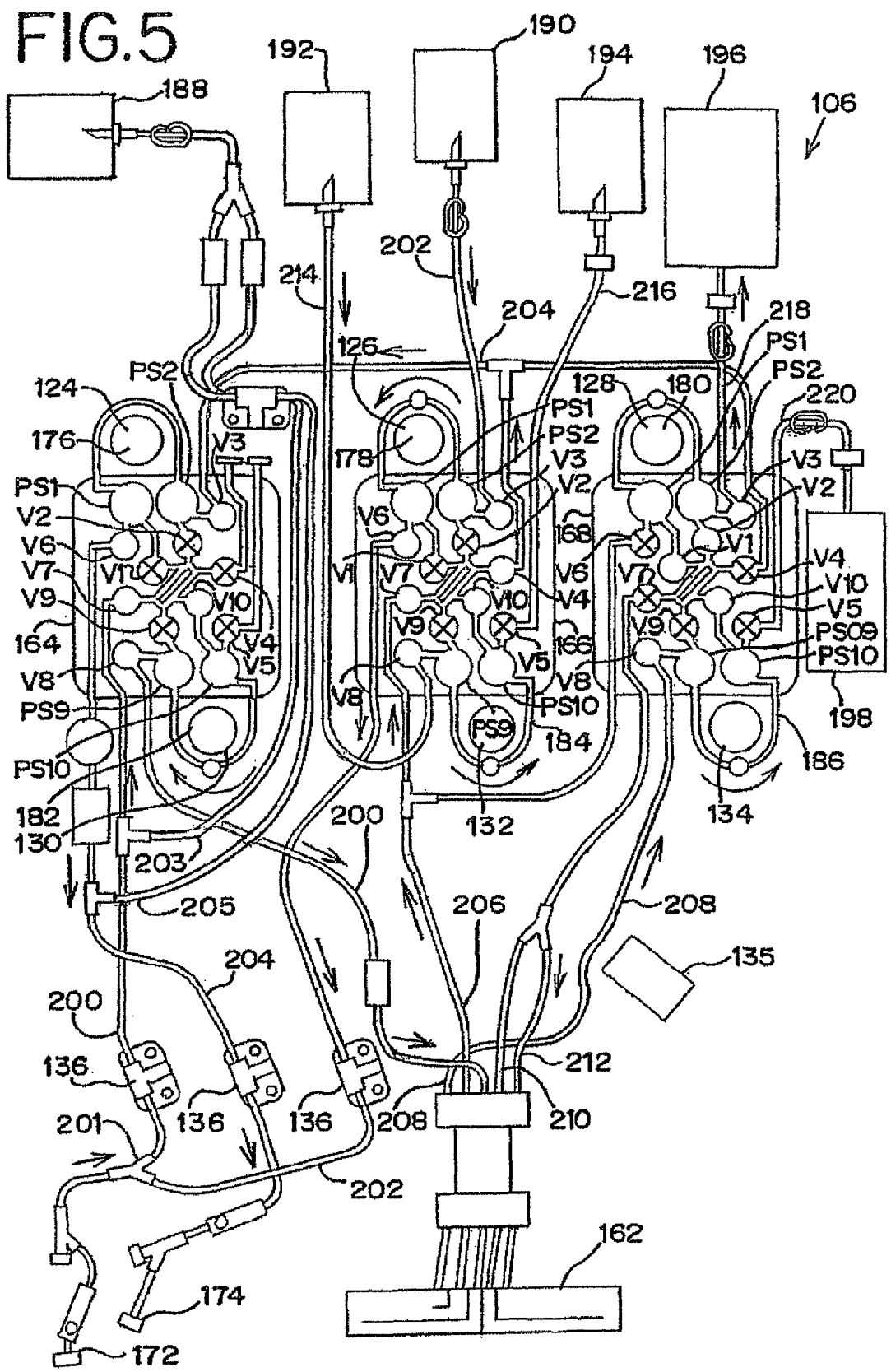
FIG. 5 is a diagrammatic view of a disposable set for use with the processing system shown in FIG. 3.

As shown in FIG. 5, each pumping cassette 164, 166, 168 has a similar internal construction and, as such, only one cassette will be described and like alpha-numeric reference characters will be used for each cassette 164, 166 and 168. In FIG. 5, the left cassette 164 includes four pressure sensing chambers PS1, PS2, PS9, and PS10 and ten valves V1, V2, V3, V4, V5, V6, V7, V8, V9, and V10, although the number and configuration of such chambers and valves are not limited to that shown and other variations are also possible including other variations for the interconnecting flow paths between such chambers and valves.

As shown in FIG. 5, each peristaltic pump 124, 126, 128, 130, 132 and 134 may be associated with a respective tubing segment 176, 178, 180, 182, 184 and 186. Also in FIG. 5, the upper pumps 124, 126 and 128 are each associated with two pressure sensing chambers PS1 and PS2 with one being located downstream and the other located upstream of the pump, depending on which direction is the desired flow direction, which direction may change, if desired, one or more times during and/or after the procedure. Similarly, the lower pumps 130, 132, and 134 are each associated with two pressure sensing chambers PS9 and PS10 located on upstream and downstream sides thereof. Such peristaltic pumps 124, 126, 128, 130, 132 and 134 are typically operated by rotation and include one or more outward extensions, roller or the like that act on the exterior of the respective tubing segments 176, 178, 180, 182, 184 and 186 to progressively compress the tubing and "push" fluid in the desired direction of flow.

Continuing to refer to FIG. 5, the set 106 also includes a saline container 188, an anticoagulant container 190, first and second replacement fluid containers 192 and 194, and first and second plasma containers 196 and 198. Preferably, each of the containers 188, 190, 192, 194, 196 and 198 is respectively associated with a corresponding weight scale 142, 144, 146, 148, and 150, and/or one of the hooks 154 shown in FIG. 3.

In FIG. 5, the set 106 further includes a first flow path 200 that fluidly communicates with the draw needle 172 for a withdrawn fluid, such as whole blood, to flow from a patient. An anticoagulant flow path 202 may communicate with the first flow path 200 at a Y-branch connector 201 to allow anticoagulant to mix with the withdrawn whole blood. Anticoagulant from the anticoagulant container 190 may be pumped to the first flow path 200 by the upper or anticoagulant pump 126 of the middle cassette 166 and flow through open valves V3 and V6 of such cassette to mix with the withdrawn whole blood.

Also in FIG. 5, the set 106 includes a second flow path 204 that fluidly communicates with the return needle 174 to allow one or more fluids, such as a replacement fluid, to flow to the patient. One or more saline flow paths 203 and 205 may also be in respective communication with the first and second flow paths 200 and 204 to allow saline flow, if desired, before, during and/or after the procedure.

By way of example and not limitation, in FIG. 5, the withdrawn whole blood flows into the first flow path 200 and through the left cassette 164 preferably through open valves V7, V10 and V8 and the lower or whole blood pump 130 of such cassette. The first flow path 200 preferably communicates with the processing chamber 162 so as to allow the withdrawn whole blood from the patient to be separated into its constituent blood components, such as red blood cells, platelets and/or plasma.

In FIG. 5, one or more outlet flow paths 206, 208, 210, and 212 may allow separated blood components, such as red blood cells, plasma and/or platelets, to separately exit the processing chamber 162. For example, separated red blood cells from the processing chamber 162 may flow through a red blood cell path 206. Separated plasma from the processing chamber 162 may flow through the plasma flow path 208. An optical detector 135 may be associated with the plasma flow path 208 to assist in optical detection of the plasma constituent.

In FIG. 5, the separated red blood cells flowing from the processing chamber 162 preferably mix with the replacement fluid and flow to the patient through the second or return flow path 204. As shown in FIG. 5, the separated red blood cells flow through the red blood cell path 206 to the middle cassette 166 and through the open valves V7 and V4 of such cassette to mix with the replacement fluid. As also shown in FIG. 5, the replacement fluid from the first replacement fluid container 192 flows through a first replacement fluid flow path 214 to the middle cassette 166. The replacement fluid may flow by operation of the lower or replacement pump 132 and flow through the open valves V8 and V10 to mix with the red blood cells downstream of the replacement pump 132 where the red blood cells and replacement fluid paths intersect. The resulting mixture of red blood cells and the replacement fluid returns to the patient by way of the second flow path 204, which path also may flow through the left cassette 164, for example, the open valves V3 and V6 of such cassette 164 shown in FIG. 5. The flow of such combined mixture to the patient may also be pumped by operation of the upper left pump 124 to aid return to the patient.

In FIG. 5, the separated plasma from the processing chamber 162 flows through the plasma flow path 208 to the first plasma container 196. Separated plasma may flow through the right cassette 168 and preferably, through the open valves V8, V10, V1 and/or V2 and V3 of such cassette 168 to a first plasma passageway 218, which flows into the first plasma container 196. Separated plasma preferably is pumped by operation of the lower or plasma pump 134 of the right cassette 168. Separated plasma may also be pumped by the upper pump 128, if desired. Each of the first and second plasma containers 196 and 198 may allow for up to about 3 liters of plasma storage. As discussed above, one or both of the first and second plasma containers 196 and 198 are preferably associated with one of the weight scales 142, 144, 146, 148, 150 for measuring the weight change of the separated plasma flowing into such container during the procedure.

In FIG. 6, separated red blood cells from the processing chamber 162 mix with the replacement fluid from the second replacement fluid container 194. A second replacement flow path 216 preferably communicates with the separated red blood cells while the first replacement flow path 214 is closed. By way of example, in FIG. 6, the second replacement flow path 216 allows flow of the replacement fluid through the opened valves V5 and V9 of the middle cassette 166 and the valves V8 and V10 are closed to stop the flow from the first replacement fluid container 192. The replacement fluid pump 132 preferably pumps such replacement fluid. As discussed above, the replacement fluid preferably mixes with the separated red blood cells downstream of the replacement pump 132 and flows through the second flow path 204 to the patient, similar to that described above. As also discussed above, each of the first and second replacement fluid containers 192 and 194 is preferably associated with a respective weight scale 142, 144, 146, 148, 150 to measure the weight change of the replacement fluid as such fluid flows from the respective container during the procedure.

In FIG. 7, the first replacement fluid flow path 214 is open to communicate with the separated red blood cells while separated plasma flows into the second plasma container 198 through a second plasma passageway 220. Such separated plasma may flow either directly from the processing chamber 162 or flow from the first plasma container 196 and/or a combination thereof. Separated plasma flowing to the second plasma container 198 may flow through the right cassette 168 such as through the open valve V5 and preferably employs operation of the plasma pump 134. It is possible that the second plasma container 198 may not be associated with a weight scale and may provide an overflow for separated plasma from the first plasma container 196, such as when the first plasma container 196 has reached its volume capacity. Separated plasma from the first plasma container 196 may flow to the second plasma container 198 until the first plasma container 196 has a sufficient volume remaining to complete the plasma exchange procedure.

FIG. 8 shows a combination of the above described fluid flows, in which the replacement fluid flows from the second replacement fluid container 194 and separated plasma flows into the second plasma container 198. Other flow patterns are also possible for the system and are not limited to those described herein. FIG. 8 also shows an alternative flow path for one of the saline flow paths 203 through the left cassette 164, and may employ use of one of the left upper or lower pumps 124 or 130, if desired, for communicating with various components of the system, depending on which valves are opened or closed. It is also possible that the saline container 188 may be used as a waste container before, during and/or after the procedure to receive one or more fluids.

OPERATION OF THE CONTROLLER

Relative to FIGS. 1-8, the controller 26 or 138 may include a programmable microprocessor that is programmed preferably to determine a commanded flow rate for the plasma and/or the replacement fluid. By way of example, in FIGS. 1-2, the operation of plasma and replacement fluid pumps 22 and 24 may be used to determine a commanded flow rate respectively for the plasma and the replacement fluid. The number of operations, such as rotations, of the respective plasma or replacement fluid pump 22 and 24 over a specified time period may be monitored by the controller 26 and multiplied by a standard pressure based calibration factor to achieve the commanded flow rate. Similarly, in FIGS. 3-8, the controller 138 may determine the commanded flow rates of the plasma and the replacement fluid by the number of rotations of the plasma (or lower right) pump 134 or the replacement fluid (or lower middle) pump 132, which respectively assist plasma and replacement fluid flow.

The controller 26 or 138 may further determine an actual flow rate for each of the plasma and the replacement fluid. In FIGS. 1-8, each actual flow rate may be determined from the measured weight change over a specified time period for each of the plasma reservoirs 12, 196, 198 or each of the replacement fluid reservoirs 14, 192, 194, each of which may be associated with their respective weight scales 16, 18, 142, 144, 146, 148 and 150. The controller 26 and 138 preferably determines such measured weight change of the plasma and replacement fluid reservoirs and multiplies such weight change by the appropriate density conversion factor for plasma or for the replacement fluid in order to achieve an actual volume change over such time period or an actual flow rate. Alternatively, if only one of the plasma containers 196 and 198, such as the first container 196, is associated with a weight scale, the controller 138 may employ the actual flow rate that was last determined with such container 196 for the duration of the plasma flow to the other container 198 that is not associated with a weight scale. The controller 138 may employ such actual flow rate, such as for purposes of fluid balance and flow rate determination, at least until the plasma flow returns to the first container 196.

In one aspect, the controller 26 or 138 preferably compares the plasma and replacement fluid commanded flow rates to their respective actual flow rates, as measured over a selected time period, for achieving the fluid balance or the net fluid volume difference of the patient. The net fluid volume difference is the difference between the fluid volume infused to the patent, such as replacement fluid volume, and the fluid volume removed from the patient, such as plasma volume, either during and/or after the plasma exchange procedure. More preferably, the controller 26 may change at least one of the plasma or replacement fluid commanded flow rates in response to a difference between the commanded flow rate and its respective actual flow rate so as to achieve such net fluid volume difference of the patient. It may be desired to maintain the net fluid volume difference of the patient within a desired range. For example, if it is desired that the patient has no net volume change, then the net fluid volume difference is about zero, such that the fluid volume infused to the patient should equal the fluid volume removed. The controller 26 or 138 thus monitors the net fluid volume difference so as to be within the desired range of about zero. The controller 26 or 138 may also take into account the anticoagulant volume added to the patient as part of the fluid volume infused to the patient and the anticoagulant container 190 is preferably associated with one of the weight scales for determining an infusion volume. Although it may be desirable to maintain a net fluid volume difference at about zero, it is possible for the controller 26 or 138 to maintain other differences, if desired. It also may be possible for the operator to specify a desired range for the net fluid volume difference before and/or during the procedure.

The controller 26 and 138 preferably monitors the net fluid volume difference of the patient at one or more times during the procedure and performs such monitoring over a selected duration of time. For example, the controller 26 or 138 may monitor the respective flow rates of the plasma and the replacement fluid on a periodic basis as often as desired during and/or after the procedure, and the duration of such monitoring may last for example, about 10 minutes, although other time intervals are also possible. Other monitoring schemes are also possible. Alternatively, the net fluid volume difference may be monitored continuously throughout the procedure, if desired.

By way of example, the net fluid volume difference for a plasma exchange procedure may generally include the amount of replacement fluid and anticoagulant infused less the amount of plasma removed, if all other components except the removed plasma are returned to the patient. The net fluid volume difference ($\Delta_{Vol}$) at any time during or after the procedure may further be expressed as:

$$\Delta_{Vol} = \text{RF Volume Infused} - P \text{ Volume Removed} + AC \text{ Volume}.$$

Where RF Volume Infused is the volume of replacement fluid infused to the patient; P Volume Removed is the volume of plasma removed from the patient; and AC Volume is the volume of anticoagulant infused to the patient.

By way of example, if the net fluid volume difference is preferred to be about zero and the plasma removed is 600 ml, or a 60 ml/min plasma flow rate over a 10 minute time interval, and 50 ml of anticoagulant is infused to the patient, or a 5 ml/min flow rate over such 10 minute interval, then the reinfusion volume is about 550 ml of replacement fluid or 550 ml=600 ml−50 ml. The resulting desired flow rate of the replacement fluid is about 55 ml/min over the same 10 minute time period.

The controller may determine a commanded flow rate of the replacement fluid based on the following ideal expression:

$$Q_{RF} = Q_P * (1 - [\text{Target Balance} - \text{Reinfusion Volume}]/\text{Total Waste Plasma}) - Q_{AC}.$$

Where $Q_{RF}$ is the commanded flow rate for the replacement fluid pump; $Q_P$ is the commanded flow rate for the plasma pump; Target Balance is the desired amount of net fluid volume change of the patient; Reinfusion Volume is a final selected amount of fluid used to push residual patient cells back into the patient; Total Waste Plasma is the amount of plasma removed; and $Q_{AC}$ is the commanded flow rate of the anticoagulant pump.

As an example, if the plasma pump commanded flow rate is about 60 ml/min and the anticoagulant flow rate is about 5 ml/min and the net fluid volume change to the patient is preferred at about zero, then the commanded flow rate for the replacement fluid pump, based on the above equation, is about 55 ml/min or $Q_{RF}$=60 ml/min−5 ml/min, assuming the plasma and replacement fluid pumps are operating at about 100% efficiency. However, if, for example, either pump is operating at an efficiency either above or below 100%, then the controller preferably may determine a commanded flow rate of the replacement fluid, based on the following expression, which take into account pump inefficiencies, as discussed above:

$$Q_{RF} = [Q_P * \text{Efficiency}_P (1 - [\text{Target Balance} - \text{Reinfusion Volume}]/\text{Total Waste Plasma}) - Q_{AC}]/\text{Efficiency}_{RF}$$

Where $\text{Efficiency}_{RF}$ is a ratio based on the actual and commanded flow rates of the replacement fluid pump; $Q_P$ is the commanded flow rate for the plasma pump; $\text{Efficiency}_P$ is a ratio based on the actual and commanded flow rates of the plasma pump; Target Balance is the desired amount of net fluid volume change of the patient; Reinfusion Volume is a final selected amount of fluid used to push residual patient cells back into the patient; Total Waste Plasma is the amount of plasma removed; and $Q_{AC}$ is the commanded flow rate of the anticoagulant pump.

For example, if the plasma pump efficiency is about 105%, the plasma pump commanded flow rate is about 60 ml/min, the anticoagulant flow rate is about 5 ml/min, the replacement pump efficiency is about 95%, and the net fluid volume change to the patient is preferred at about zero, then the commanded flow rate of the replacement fluid is preferably about 61.05 ml/min or (60 ml/min*1.05−5 ml/min)/0.95. Thus, the actual flow rate of the replacement pump is about 58 ml/min=61.05 ml/min*0.95. The actual flow rate of the plasma pump is about 63 ml/min=60 ml/min*1.05. By way of example, during a 10 minute period, 580 ml of replacement fluid and 50 ml of anticoagulant may be infused to the patient and 630 ml of plasma is removed from the patient such that a net fluid volume difference of the patient is about zero or $\Delta_{Vol}$=580 ml−630 ml+50 ml. It is understood that the above example is for illustrative purposes and is not intended to limit the present disclosure.

In another aspect, the controller 26 or 138 may also determine the commanded and actual flow rates for one or both of the plasma or the replacement fluid so as to achieve a desired flow rate. By way of example, the controller 26 or 138 may determine the commanded and actual flow rates for one or both of the plasma and the replacement fluid pumps, over a selected time period, so as to determine whether a desired flow rate is achieved for such time period. Such controller 26 or 138 preferably may determine such flow rates based on a periodic time period, such as about every 1 to 2 minutes. Other time period intervals are also possible as well as time intervals based on a specific plasma or replacement fluid weight (or volume) change. It is also possible for the controller to continuously compare such flow rates if desired.

For example, the controller 26 or 138 may determine the commanded and actual flow rates of the plasma pump 22 or 134 over a selected time period to be about 30 ml/min and 32 ml/min, respectively. The resulting plasma pump efficiency is about 107%. If the desired plasma pump flow rate is about 30 ml/min, then the controller 26 or 138 may decrease the commanded plasma flow rate to about 28 ml/min (or a correction factor of about 0.94) so as to compensate for the plasma pump inefficiency and achieve the desired flow rate, e.g., 30 ml/min=28 ml/min*1.07. Alternatively, the controller 26 or 138 may adjust the flow rate of the replacement fluid to correct the fluid balance difference to the patient and may proportionally increase the replacement fluid commanded flow rate so as to maintain the patient's fluid balance.

Using the same example above, the controller 26 or 138 may determine the commanded and actual flow rates of the replacement fluid pump 24 or 132 over the same time period to be about 30 ml/min and 28 ml/min, respectively. The replacement fluid pump efficiency is about 93%. If the desired replacement fluid pump flow rate is about 30 ml/min, then the controller 26 or 138 may increase the replacement fluid commanded flow rate to about 32 ml/min (or a correction factor of about 1/0.93 or 1.07) so as to compensate for the replacement fluid pump inefficiency and achieve the desired flow rate. Alternatively, the controller may proportionally decrease the plasma pump commanded flow rate. It is also possible that the controller 26 or 138 may determine the operating efficiency of the anticoagulant pump 126 and adjust the flow rate thereof and/or any of the other pumps 124, 130 or 128 operating during the procedure.

The controller 26 or 138 may also monitor each weight scale to mitigate the effect of any external disturbances by the operator, patient and/or other factors. For example, the controller 26 or 138 may monitor each scale for the extent of weight change during each one-second time interval. If there is a weight change during a particular one second time interval that is greater than a set limit, then the controller 26 or 138 may disregard such change as due to an external disturbance to the scale that is not the result of an actual weight change of the plasma or replacement fluid. It is also possible that such disturbance may trigger an alarm that halts the procedure until the disturbance is cured by the operator. Alternatively, the controller may employ use of a plasma or replacement fluid container on another scale that is not affected by such disturbance.

The controller 26 or 138 may also control the commanded flow rate of the plasma pump 22 or 134 based, at least in part, on a radial position of the plasma and red blood cells interface in the separator 8 or processing chamber 162. For example, the controller 26 or 138 may control the commanded plasma flow rate, at least in part, based on a desired flow rate that maintains the interface at a desired radial location, which allows the separated plasma, red blood cells and/or remaining blood components to exit the separator 8 or the processing chamber 162 along their desired flow paths.

In a further aspect, a method for controlling a net fluid volume difference of the patient may be employed with any of the above described embodiments. The method may include monitoring a first flow rate of at least a first fluid, such as plasma that is removed from the patient as part of the withdrawn whole blood, and a second flow rate of at least a second fluid, such as a replacement fluid, flowing to the patient. As discussed above, the commanded flow rates of the plasma and the replacement fluid may be respectively determined, at least in part, by the number of pump operations over a time period. For example, the operations of the plasma and replacement pumps 22, 24, 132, 134 may be monitored over a specific time period to achieve such commanded flow rate. The method may also include determining an actual flow rate for each of the plasma and replacement fluid, based, at least in part, on an actual volume of such plasma removed from the patient and such replacement fluid flowing to the patient. For example, the actual volume may be determined by the measured weight change of the respective plasma and replacement fluid reservoir over the specified time period. The method may further include changing at least one of the plasma and replacement fluid commanded flow rates so as to achieve a desired net fluid volume difference of the patient. The desired net fluid volume difference may be controlled with a desired range and may, for example, be about zero although other desired ranges are possible.

In yet a further aspect, a method for controlling a flow rate of at least one fluid, such as the plasma or the replacement fluid, may be employed using any of the above described embodiments. The method may include determining a commanded flow rate of at least one of a first fluid flowing to a patient or a second fluid flowing from a patient, where the first fluid preferably includes a replacement fluid and the second fluid preferably includes plasma. As previously discussed above, the commanded flow rate of the plasma or the replacement fluid may be based, at least in part, on a calculated volume of such plasma or replacement fluid that flows over a time period. For example, the calculated volume may be based on a number of operations, such as rotations or pulsations, of the plasma or replacement pump over such time period. The method may also include determining an actual flow rate of the plasma or the replacement fluid based, at least in part, on an actual volume that respectively flows over such time period. As discussed above, such actual volume may be based on a measured weight difference of the plasma or the replacement fluid reservoir over such time period. The method may further include changing the commanded flow rate of the plasma or the replacement fluid in response to a difference between the commanded flow rate and the actual flow rate to achieve a desired flow rate.

As can be seen from the above description, the present disclosure has several different aspects, which are not limited to the specific structures shown in the attached drawings. Variations of these concepts or structures may be embodied in other structures for carrying out other applications in the medical or other fields without departing from the present invention as set forth in the appended claims.

What is claimed is:

1. A system for controlling a net fluid volume difference of a patient during and/or after a medical fluid exchange procedure including:
   a first flow path for flowing at least a first fluid from the patient;
   a second flow path for flowing at least a second fluid to the patient;
   first and second reservoirs respectively associated with the first and second flow paths; and
   a programmable controller associated with the first and second flow paths for controlling the flow of the first and second fluids at respective first and second commanded flow rates including first and second pumps, such controller operable to determine an actual flow rate for each of the first and second fluids based, at least in part, on an actual volume difference respectively measured relative to the first and second reservoirs over a time period; such controller operable to change at least one of the first and second commanded flow rates in response to a difference between at least one of the first and second commanded flow rates and its respective actual flow rate so as to achieve a net fluid volume difference of the patient, the controller being configured to monitor the number of pump operations of the respective first and second pumps over a time period and multiply said numbers by a standard pressure-based calibration factor, and the controller further being configured to determine the first and second commanded flow rates based thereon.

2. The system of claim 1 wherein the controller determines the actual volume difference of the first and second fluids based, at least in part, on a measured weight difference of the respective first and second reservoirs over the time period.

3. The system of claim 1 wherein the controller is programmable and is programmed to control the net fluid volume difference within a desired range.

4. The system of claim 1 wherein the net fluid volume difference is about zero.

5. The system of claim 1 wherein the first fluid includes plasma and the second fluid includes a replacement fluid.

6. A system for controlling a flow rate of at least one fluid flowing during a fluid exchange procedure including:
a first flow path for flowing at least a first fluid from a patient;
a second flow path for flowing at least a second fluid to the patient, wherein the first and second fluids include selected one of plasma or a replacement fluid;
first and second reservoirs respectively associated with the first and second flow paths; and
a programmable controller associated with the first and second flow paths for controlling the flow of the first and second fluids including first and second pumps, such controller operable to determine a commanded flow rate of at least one of the first and second fluids based, at least in part, on a calculated volume of such first or second fluid that flows through its respective flow path over a time period and further operable to determine an actual flow rate of such first or second fluid based, at least in part, on an actual volume difference respectively measured relative to the first or second reservoir over such time period, such controller operable to change such commanded flow rate in response to a difference between the commanded flow rate and the actual flow rate to achieve a desired flow rate, the controller being configured to monitor the number of pump operations of the respective first and second pumps over a time period and multiply said numbers by a standard pressure-based calibration factor, and the controller further being configured to determine the first and second commanded flow rates based thereon.

7. The system of claim 6 wherein the controller determines the actual volume difference of the first or second fluid based, at least in part, on a measured weight difference of the respective first or second reservoir over the time period.

8. The system of claim 6 wherein the controller determines the commanded and actual flow rates for both of the first and second fluids.

* * * * *